(12) United States Patent
Campa, III

(10) Patent No.: US 9,205,105 B2
(45) Date of Patent: Dec. 8, 2015

(54) INDICATION AND TECHNIQUE FOR THE USE OF CROSS-LINKED HYALURONIC ACID IN THE MANAGEMENT OF PAIN

(71) Applicant: John Ascencion Campa, III, Albuquerque, NM (US)

(72) Inventor: John Ascencion Campa, III, Albuquerque, NM (US)

( * ) Notice: Subject to any disclaimer, the term of this patent is extended or adjusted under 35 U.S.C. 154(b) by 5 days.

(21) Appl. No.: 14/166,209

(22) Filed: Jan. 28, 2014

(65) Prior Publication Data

US 2014/0349958 A1    Nov. 27, 2014

Related U.S. Application Data

(60) Provisional application No. 61/826,199, filed on May 22, 2013.

(51) Int. Cl.

| | |
|---|---|
| *A61K 31/728* | (2006.01) |
| *A61K 31/167* | (2006.01) |
| *A61K 9/00* | (2006.01) |
| *A61K 9/06* | (2006.01) |
| *A61K 9/08* | (2006.01) |
| *A61K 9/70* | (2006.01) |

(52) U.S. Cl.
CPC .............. *A61K 31/728* (2013.01); *A61K 9/0009* (2013.01); *A61K 9/0014* (2013.01); *A61K 9/0019* (2013.01); *A61K 9/0024* (2013.01); *A61K 9/06* (2013.01); *A61K 9/08* (2013.01); *A61K 9/7023* (2013.01); *A61K 31/167* (2013.01)

(58) Field of Classification Search
CPC  A61K 31/728; A61K 31/167; A61K 2300/00
USPC ...................................... 514/54; 604/20, 506
See application file for complete search history.

(56) References Cited

U.S. PATENT DOCUMENTS

| | | |
|---|---|---|
| 4,920,982 A | 5/1990 | Goldstein |
| 2003/0152637 A1* | 8/2003 | Chasin et al. ................. 424/501 |
| 2006/0030899 A1 | 2/2006 | O'Keeffe et al. |
| 2006/0040894 A1 | 2/2006 | Hunter et al. |
| 2009/0035250 A1 | 2/2009 | Drapeau et al. |
| 2009/0155314 A1 | 6/2009 | Tezel et al. |
| 2009/0211294 A1 | 8/2009 | Carey et al. |

OTHER PUBLICATIONS

Pacini et al. Pulsed current iontophoresis of hyaluronic acid in living rat skin. J Dermatol Sci 44:169-171, 2006.*
Fulton et al. Filler injections with the blunt-tip microcannula. J Drugs Dermatol 11:1098-1103, Sep. 2012.*
International Search Report dated Sep. 23, 2014 from corresponding international application PCT/US2014/039151 USPTO PCT Division/ Authorized Officer Lee W. Young.

* cited by examiner

*Primary Examiner* — Mark Shibuya
*Assistant Examiner* — Yih-Horng Shiao
(74) *Attorney, Agent, or Firm* — Plager Schack LLP

(57) ABSTRACT

A method of treating pain involves administering to a human in need of such treatment a therapeutically effective amount of hyaluronic acid. In some embodiments, the hyaluronic acid is a non-avian based non-cross linked hyaluronic acid configured to treat post-traumatic and degenerative joint disorders. In some embodiments, the hyaluronic acid is cross linked hyaluronic acid.

15 Claims, 4 Drawing Sheets

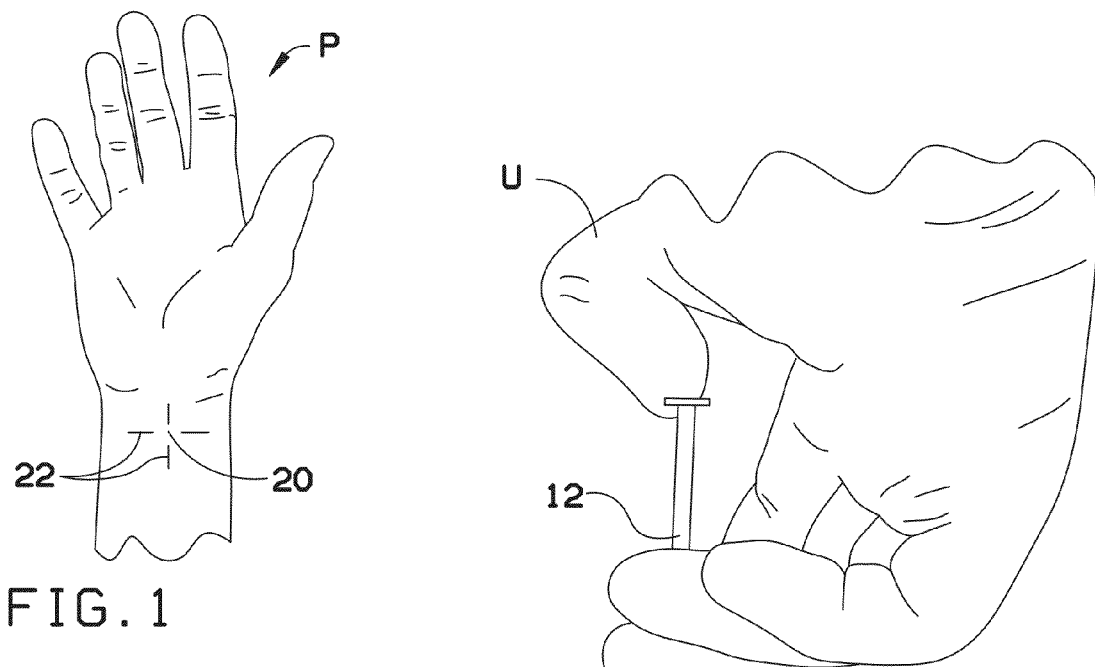
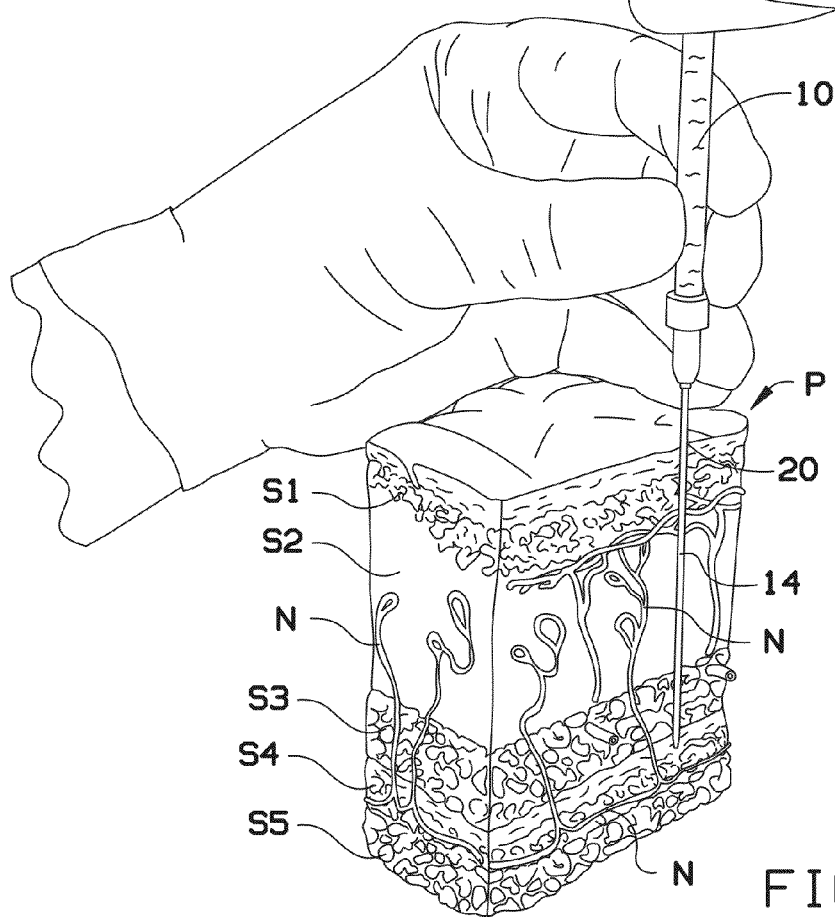
FIG. 1
FIG. 2

INDICATION AND TECHNIQUE FOR THE USE OF CROSS-LINKED HYALURONIC ACID IN THE MANAGEMENT OF PAIN

RELATED APPLICATION

This application claims priority to provisional patent application U.S. Ser. No. 61/826,199 filed on May 22, 2013, the entire contents of which is herein incorporated by reference.

BACKGROUND

The embodiments herein relate generally to uses for cross-linked hyaluronic acid.

Persistent or chronic pain is a worldwide problem affecting millions of people, including the patient and family, marriage, and employer. This places a huge burden upon a country's healthcare system, resulting in billions of dollars spent annually in diagnosis, treatment, surgery, medications, rehabilitation as well as lost wages and productivity. Embodiments of the present invention involve a new indication of cross-linked hyaluronic acid for treating pain.

As noted in U.S. Pat. No. 3,396,081 issued to Billek, hyaluronic acid is a naturally existing composition of matter that can be found in the eyes and umbilical cords of mammals and extracted in a number of ways including precipitation with acetone to create a dry powder.

As noted in U.S. Pat. No. 4,716,224 issued to Okuyama, cross-linked hyaluronic acid is obtainable by crosslinking hyaluronic acid with a polyfunctional epoxy compound selected from halomethyloxirane compounds, compounds of the formula:

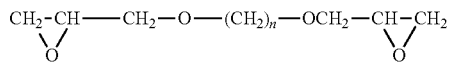

wherein n is from 2 to 6, and diglycidyl ethers of bisphenol A or bisphenol F, said crosslinked hyaluronic acid or salt exhibiting water solubility and having a crosslinking index of 5 or more per 1000 repeating disaccharide units composed of glucuronic acid and N-acetylglucosamine.

The properties of hyaluronic acid were first determined by Karl Meyer in 1930. In particular, it is an anionic, nonsulfated glycosaminoglycan found throughout connective, epithelial, and neural tissues. As such, is it known to be a disaccharide polymer, composed of D-glucuronic acid and D-N-acetylglucosamine, linked via alternating $\beta$-1,4 and $\beta$-1,3 glycosidic bonds. It may be 25,000 disaccharide pairs in length, hence, it can range in molecular weight from 5,000 to 20,000,000 daltons; the foregoing considered, then hyaluronic acid's microdensity and its negative molecular charge will be greatly increased by further increasing its cross-linkage. This in turn, will directly affect its impact on the known cell receptors, for example, intercellular adhesion molecule-1 (ICAM-1). ICAM-1 is also believed to modulate inflammatory activation.

As used in this application, "non-cross linked hyaluronic acid" generally means refined forms of the naturally existing compounds. Also, "cross linked hyaluronic acid" means hyaluronic acid crosslinked with a polyfunctional epoxy compound. Further, "hyaluronic acid" refers to both non-cross linked hyaluronic acid and cross linked hyaluronic acid.

Embodiments of the present invention are simpler, safer, economical, more reliably enduring and effective at treating pain than the prior art. As there is no systemic absorption into the blood stream with the doses recommended, there is no potential for any related impaired cognition, psychotomimetic effects, or cardiovascular and/or cerebrovascular threat or instability; hence, rehabilitation may proceed unfettered.

SUMMARY

A method of treating pain which comprises administering to a human in need of such treatment a therapeutically effective amount of hyaluronic acid. In some embodiments, the hyaluronic acid is a non-avian based non-cross linked hyaluronic acid configured to treat post-traumatic and degenerative joint disorders. In some embodiments, the hyaluronic acid is cross linked hyaluronic acid.

In some embodiments, administering to a human includes the following steps. First, locating a peripheral nerve that is supplying sensation to a painful or an impaired body part. Next, determining a most reactive neural point overlying the peripheral nerve that produces a paresthesia in a painful area. Then, isolating and marking an injection site with target marking lines at a reactive neural point overlying the peripheral nerve. Following that, preparing an epidermis with alcohol and performing a skin wheal with a local anesthetic. In some embodiments, the local anesthetic is 2% Lidocaine.

In some embodiments, the method further comprises: performing a test injection with syringe filled with a compound to verify proper nerve selection. That compound can be a 2% plain Lidocaine and 0.25% plain Bupivacaine. Then, inserting a needle attached to the syringe filled with cross-linked hyaluronic acid through the skin wheal and past a reactive point. Next, injecting the cross-linked hyaluronic acid proximate the peripheral nerve. In some embodiments, the needle is an atraumatic microcannulas having one, two or three side ports. In some embodiments, a volume of cross-linked hyaluronic acid is 0.05-0.1 cc per aliquot.

In some embodiments, the method includes introducing a regional nerve block; and utilizing a stimulator-guided local anesthetic and a cross linked hyaluronic acid delivery system. System settings in the stimulator-guided local anesthetic and cross linked hyaluronic acid delivery system are: output range of 0-5 mA; pulse width of 0.1 msec; stimulation frequency of 1 Hz; polarity positive and amperage is between 2.5 mA and 3 mA.

In some embodiments, administration is accomplished via an electromotive drug administration. In some embodiments, administration is accomplished via transdermal drug delivery system. In some embodiments, administration is accomplished via an implantable drug reservoir and delivery system.

BRIEF DESCRIPTION OF THE FIGURES

The detailed description of some embodiments of the invention will be is made below with reference to the accompanying figures, wherein like numerals represent corresponding parts of the figures.

FIG. 1 shows marking a patient for an injection;

FIG. 2 is a detail section view, illustrating the insertion of the needle;

DETAILED DESCRIPTION OF CERTAIN EMBODIMENTS

The present application discloses that the substantial increase in negative charge in hyaluronic acid will have a direct inhibiting effect on the nerve action potential, especially the small C-fibers found in the skin, effectively rendering it blocked, varying from partial to complete, as a function of the treated tissue region's negative hyperpolarization state. This latter effect likely explains, in great part, its immediate pain relieving effect.

These properties of microdensity and negative polarization that follows increasing cross-linkage and/or varying the particular disaccharide moieties can be modified as noted below to be effective in a variety of applications.

Below disclosed are examples of a method of treating pain and other conditions which involve administering to a human in need of such treatment a therapeutically effective amount of cross-linked hyaluronic acid or non-cross linked hyaluronic acid. These examples are provided to explain embodiments of the present invention and are not intended to be exclusive.

Example 1

Injection

By way of example, and referring to FIG. 1, one embodiment of the present method comprises first assessing patient P to determine peripheral nerve N supplying sensation to the painful or impaired body part. Next, examining patient P and then isolating and marking injection site 20 with target marking lines 22 by determining a most reactive neural point overlying nerve N that produces a paresthesia in the painful area.

In some embodiments, user U can refine the reactive point using a metallic blunt, five inch long, ¼ inch diameter probe (e.g., telescoping pointer), exerting slow, but steadily increasing pressure over the previously determined reactive point to more precisely determine the angle of intended needle penetration and depth, at which point when probed, reproduces the limiting pain and/or paresthesia. An objective of this can be to have the target nerve be directly under the head of the probe. To more precisely determine this point, first gently elicit the painful paresthesia, then move the probe one probe width (i.e., ¼ inch) medially, elicit the paresthesia and ask the patient how it compares to the original point, then return to center, and move one probe width laterally and elicit paresthesia, and ask the patient to compare again and return to center. And so on, moving the probe to elicit and score the paresthesias to the remaining superior (cephalad) and inferior (caudad) positions, all one probe width from center. The user can then select the most reactive probed site 20 and mark with final targeting marks 22.

Figure 3:
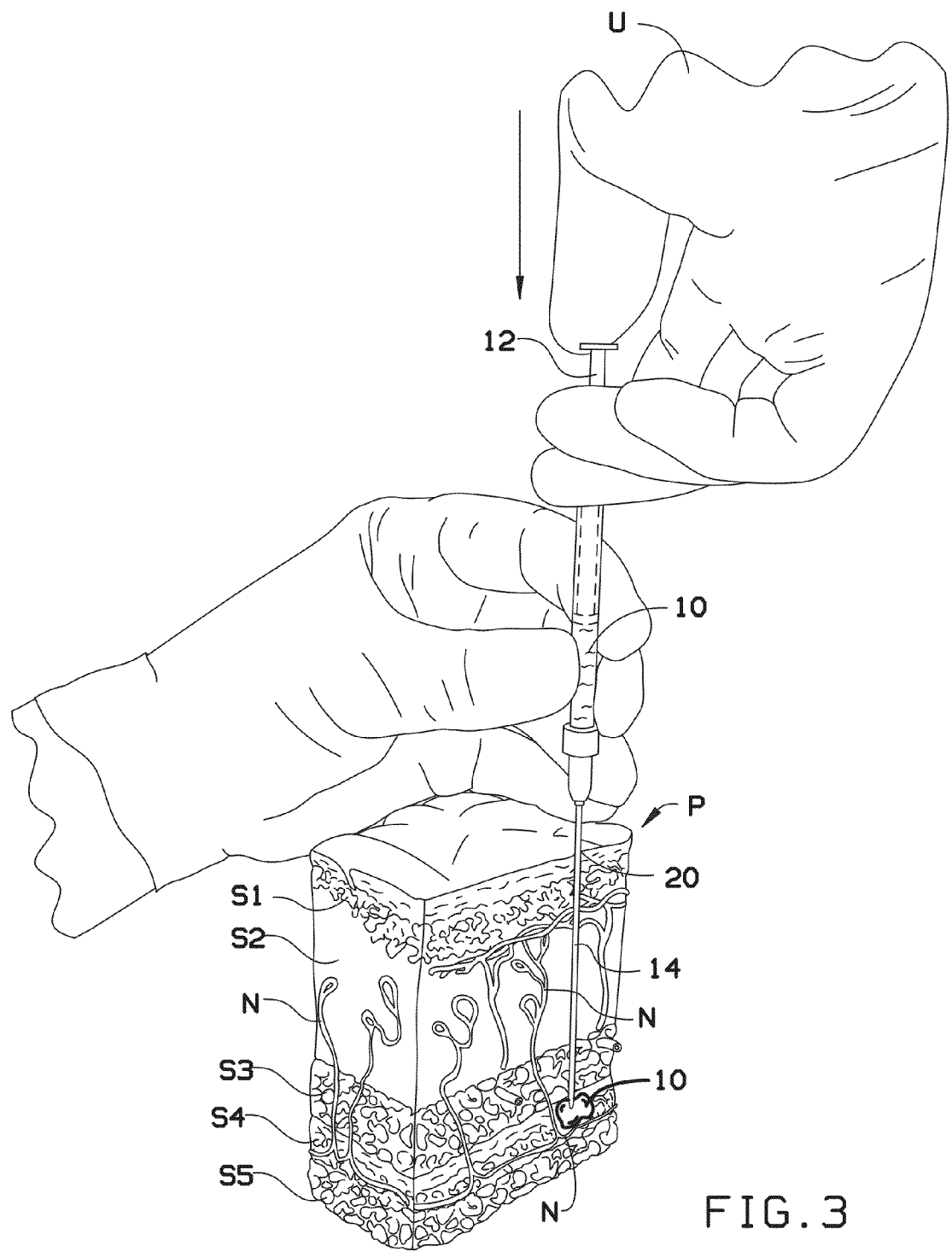
FIG. 3 is a detail section view, illustrating the injecting of the compound.
Figure 4:
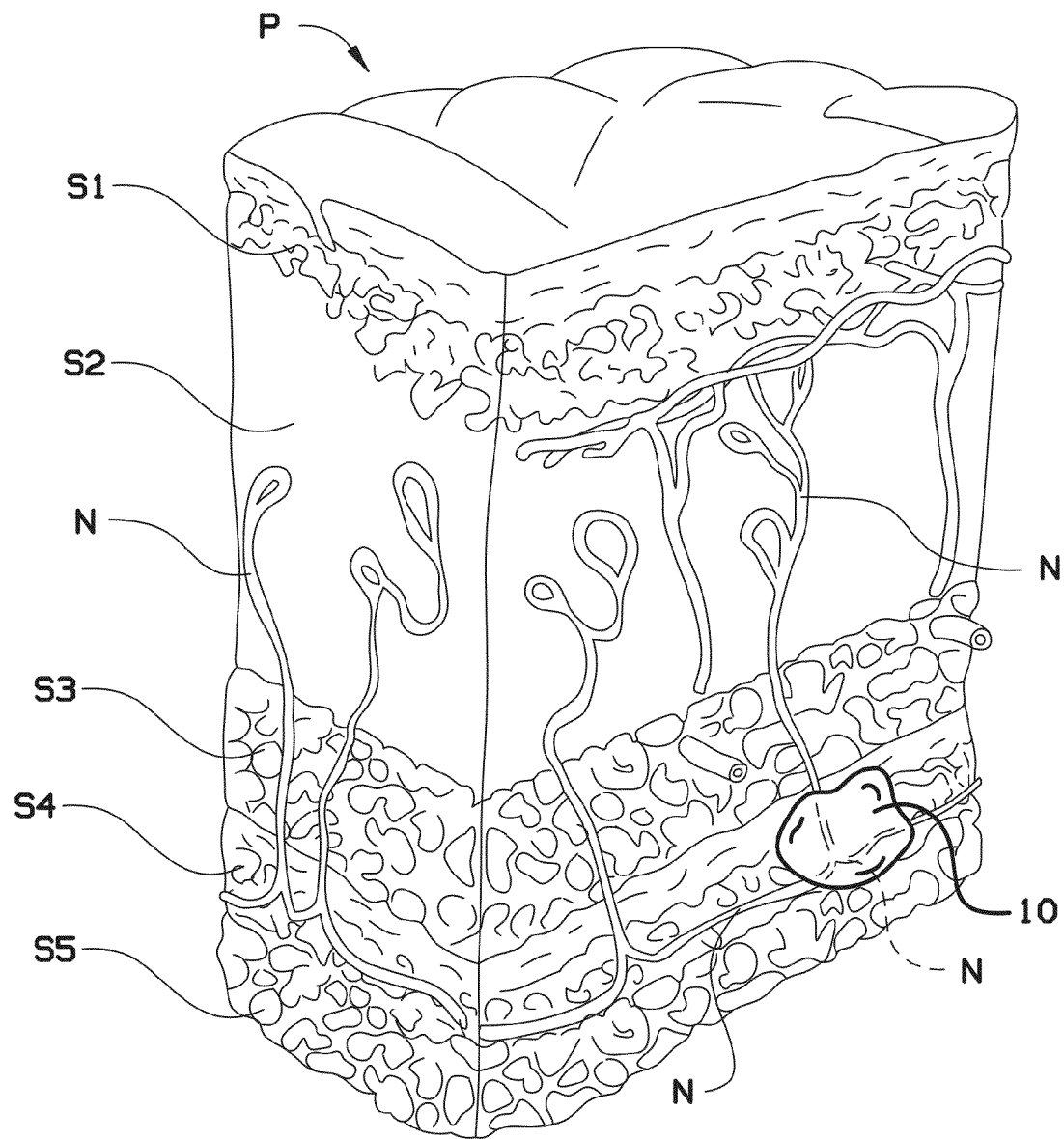
FIG. 4 is a detail section view, illustrating the compound enveloping the fascia layer
Figure 5:
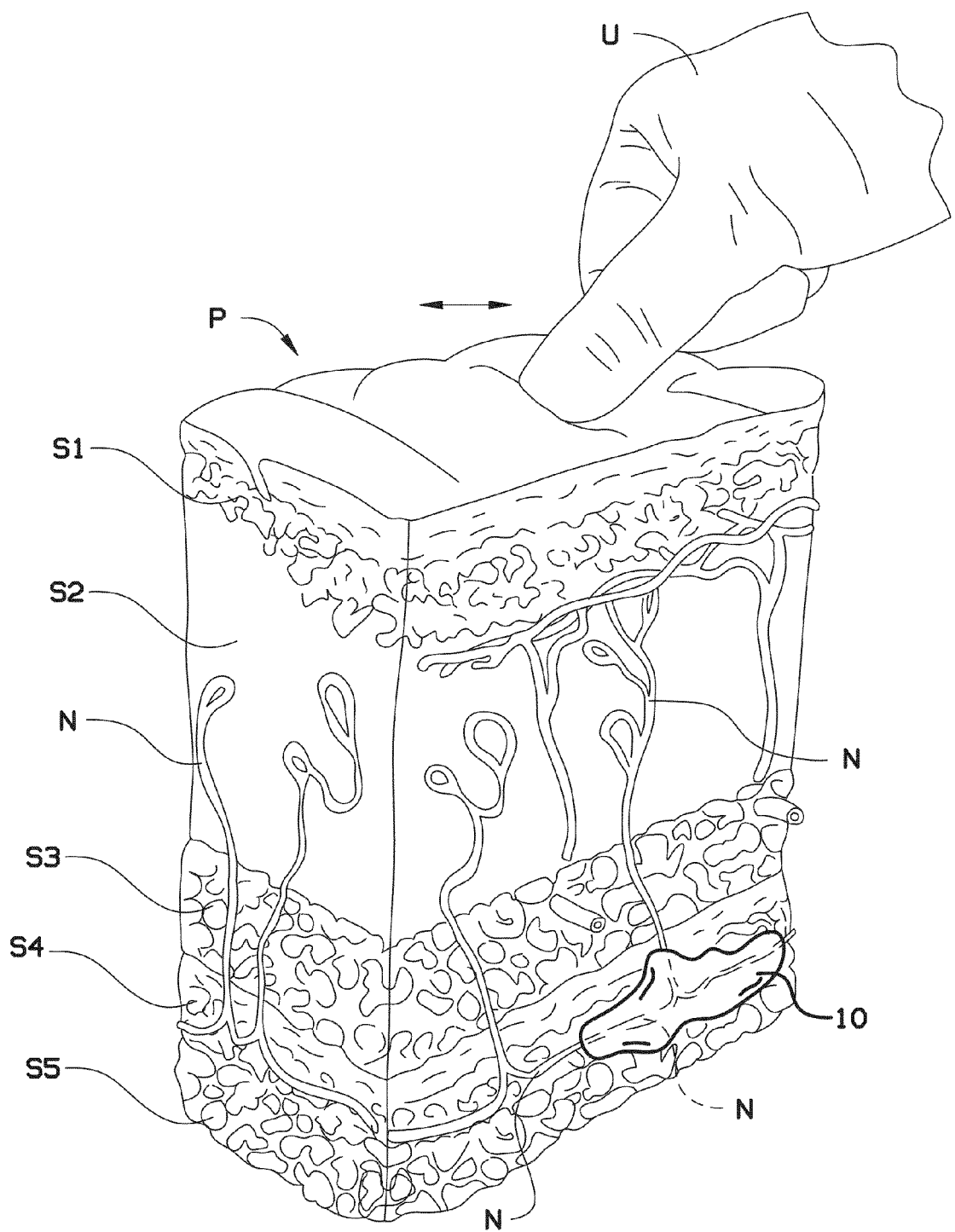
FIG. 5 is a detail section view, illustrating the spreading of the compound in reaction to the operator.

Turning to FIG. 3, FIG. 4 and FIG. 5, patient P has skin arranged as follows. Epidermis S1 is immediately adjacent to dermis S2. Dermis S2 is further immediately adjacent to subcut layer S3. Subcut layer S3 is further immediately adjacent to fascia layer S4. Fascia layer S4 is further immediately adjacent to muscle layer S5. Nerves N travel through muscle layer S5 and extend upward through fascia layer S4, subcut layer S3 into dermis S2, in patterns that are well known in medical literature. In non-humans, the anatomy is slightly different, but suffice it to say there are nerves N beneath the surface. As used below, compound 10 is in syringe 12.

Returning to an embodiment of the disclosed method, user U would prepare epidermis S1 with alcohol and perform a skin wheal (or skin wheals) with a local anesthetic such as 2% plain Lidocaine. The user performs a test injection to verify proper nerve N selection and pain relief by having compound 10 be a 50/50 mixture of 2% plain Lidocaine and 0.25% plain Bupivacaine inserted into syringe 12. Injectate 10 volumes used for this step may range from 0.5 cubic centimeters (cc) to 5 cc. Introduce needle 14, attached to syringe 12, to the depth of the appropriate tissue plane and injection compartment, and monitor injectate 10 and/or a needle induced paresthesia.

After this the user slowly injects an appropriate volume, the volume is a function of the nerve caliber and virtual size and yield of the injection compartment, of the Lidocaine/Bupivacaine mixture 10, 0.5-1 cc per aliquot, allowing a few seconds in between for medication tissue diffusion.

At 15 minutes post-injection, there should be at least 80% or greater pain relief to verify that cross-linked hyaluronic acid injection will render the expected therapeutic response, i.e., a positive test. Otherwise, a different nerve must be selected, the test injection repeated, until either 1) proper relief is obtained with simple local anesthetic mixture; 2) correct nerve N selection is verified and 3) a location for nerve N is documented in the record.

Once verified, patient P is informed that the preliminary pain relief of the test injection will usually last from four hours to four days, and will wear off. When usual or baseline pain of patient P has returned (i.e., approximately one week later), patient P is brought back and the cross-linked hyaluronic acid injection is then performed over the previously documented nerve N.

For cross-linked hyaluronic acid injection user U selects injection syringe 12 is then coupled to an appropriate gauge and length hypodermic needle (e.g., 27 G, 1½ inch) and introduced through the wheal. The user should select a needle that will be approximately one inch longer that the estimated depth of tissue to reach the reactive point. In certain circumstances (e.g., very superficially placed cutaneous nerve) use of a blunt tip, side ported microcannula may be appropriate, which will require a sharp tipped introducer, at least a gauge larger than the selected microcannula gauge to permit easy entry. The microdensity of the cross-linked hyaluronic acid selected should be in keeping with the width and breadth of the injection compartment where injectate 10 will be deposited, e.g., use a less dense formulation with smaller injection compartments, to allow for injectate 10 expansion at 24 hours due to water absorption from adjacent tissues, or a more dense and viscous formulation to fill in larger injection compartments.

For cross-linked hyaluronic acid injection user U introduces a needle, attached to syringe 12, to the depth of the appropriate tissue plane and injection compartment, and monitor injectate 10 and/or a needle induced paresthesia. The user slowly injects an appropriate volume and microdensity (the volume and microdensity are a function of the nerve caliber and virtual size and yield of the injection compartment) of the cross-linked hyaluronic acid, 0.05-0.1 cc per aliquot, allowing a few seconds in between each injection. The user then withdraws needle 14 and gently massages the skin overlying the injected area in the direction of the long-axis of treated nerve N, both proximally and distally, for 0.75 cm.

User U can then cover injection site 20 with an adhesive bandage. Pain relief often is immediate, but can take up to 5-10 minutes to develop, with an expected duration (with current microdensities) of three to six months.

User U should advise patient P of hyaluronic acid's inherent water absorption properties over 24 hours and post-procedure precautions, e.g., no prolonged physical activity, heat exposure or alcohol consumption for 24 hours.

Example 2

Stimulator-Guided Local Anesthetic and Cross Linked Hyaluronic Acid Delivery System When using a stimulator-guided local anesthetic and cross linked hyaluronic acid delivery system (e.g., model NL-III Tracer nerve locator), the skin is whealed and prepared with a 16-G, 2.5 cm introducer. Then an HN3 40-80 mm, 22 G, insulated regional nerve block needle is introduced. Stimulator settings are: Output range of 0-5 mA; Pulse width of 0.1 msec; Stimulation frequency of 1 Hz; Polarity positive. Effective stimulation is usually achieved with a milliampere setting of 2.5-3 mA. After the nerve is isolated and identified electrically, 0.5-1.5 cc of injectate 10 is introduced as indicated in example 1.

Example 3

Iontophoresis

In certain cases where pain covers a wide area, such as burned torso, a machine, similar to those employed to effect iontophoresis also called electromotive drug administration (EDMA), may be used to administer, the cross-linked hyaluronic acid into the exposed and healing tissues, without the use of a needle.

Example 4

Transdermal Delivery System

The cross-linked hyaluronic acid may be embedded into a transdermal drug delivery system such as a medicated skin patch to form a topical vehicle of administration over the painful area.

Example 5

Nucleus Pulposus Tamponade and Injection—Intradiscal Analgesia, Restoration and Rejuvenation By modification of hyaluronic acid's properties of microdensity and negative polarization that follows increasing cross-linkage and/or varying the particular disaccharide moieties, the hyaluronic acid may be placed at the core of a damaged or degenerated (aging) spinal disc (i.e., nucleus pulposus), providing immediate pain relief, physician-assisted reconstitution of the nucleus, and eventual restoration of disc related loss of height, or intervertebral disc space. This latter phenomenon can result in decrease of adjacent nerve root impingement, with restoration of nerve root function. For instance there could be improved motor and sensory function, as well as relief of impingement related pain.

Example 6

Intra-Articular and Periarticular Injection—for Joint Analgesia, Restoration and Rejuvenation By modification of hyaluronic acid's properties of microdensity and negative polarization that follows increasing cross-linkage and/or varying the particular disaccharide moieties, the hyaluronic acid may be injected intra-articularly and peri-articularly into a damaged or degenerated (aging) joint that could be created from conditions such as osteoarthritis and rheumatoid arthritis. This provides immediate pain relief, physician-assisted reconstitution of the joint space, and eventual restoration of joint space height.

Example 7

Cosmetic Prolonged Duration Cross-Linked Hyaluronic Acid Dermal Fillers

By modification of hyaluronic acid's properties of microdensity and negative polarization that follows increasing cross-linkage and/or varying the particular disaccharide moieties, the hyaluronic acid may be developed and used as a new and improved form of hyaluronic acid based cosmetic dermal filler. For example, there may be a much longer duration of effect and significantly reduced injection related pain during administration.

Example 8

Cosmesis and Surgical Reconstruction Appliance

By modification of hyaluronic acid's properties of microdensity and negative polarization that follows increasing cross-linkage and/or varying the particular disaccharide moieties, the hyaluronic acid may be placed at the core of an implantable cosmetic appliance. This would assist in the surgical correction of a disfiguring and/or a painful and limiting defect.

Example 9

Cross-Linked Hyaluronic Acid and Non-Cross-Linked Hyaluronic Acid as an Adjunct to Expedite Chronic Wound Healing By modification of hyaluronic acid's properties of microdensity and negative polarization that follows increasing cross-linkage and/or varying the particular disaccharide moieties, the hyaluronic acid may be developed and used as an adjunct to expedite the healing of chronic wounds, which inherently depend upon adequate blood flow, which would be optimized by enhanced C-fiber neural function. By administering the hyaluronic acid either proximal to, over the wound or into the wound bed, so that it surrounds those C-fibers responsible for modulating wound blood circulation, the increased delivery of oxygen and nutrients would promote enhanced healing. Additionally, as blood flow is now optimized, venous drainage would also be secondarily improved, resulting in accelerated drainage of the wound's metabolic waste products, toxins, and $CO_2$—further promoting wound healing.

Example 10

Implantable Pump Delivery System

An implantable drug reservoir and delivery system or pump, may be developed to provide long term release of the cross-linked hyaluronic acid, when a more constant level of the drug is required.

Example 11

Specialized Atraumatic Microcannulas (Blunt Tip Needle) for Cross-Linked Hyaluronic Acid Injection By modifying currently available blunt tip microcannulas, a more efficient injection process may be developed. For instance, to maintain the blunt tip, but decrease the width of the current side port, and increase the number of side ports from one, to two or three. This would provide for a more even distribution of the cross-linked hyaluronic acid in the injection compartment, as well as decrease the total injection time, as more drug is delivered more quickly through multiple ports. Additionally, this can then be adapted to an appropriate stimulus delivery device (stimulator-guided injection), for more precise localization of the target nerve, where necessary.

Example 12

Topical Cream

By modification of hyaluronic acid's properties of microdensity and negative polarization that follows increasing cross-linkage and/or varying the particular disaccharide moieties, the hyaluronic acid may be formulated as the active ingredient of a topically applied cream, useful for burns, aches, pains and strains.

Example 13

Non-Cross Linked Hyaluronic Acid Use in Pain Management, Neuromuscular Rehabilitation and Sports Related Injuries By modification of hyaluronic acid's properties of microdensity and negative polarization that follows increasing cross-linkage and/or varying the particular disaccharide moieties, an improved form may be created and used in pain management, neuro muscular rehabilitation and sports related injuries.

Example 14

Non-Cross Linked Hyaluronic Acid Use in Intra-Articular Joint Disorders

By modifying a non-avian based non-cross linked hyaluronic acid to change properties of microdensity and negative polarization, an improved form may be created and used in treating post-traumatic and degenerative joint disorders, with increased duration of effect, and more immediate pain relief.

With minor modifications, its use in veterinary medicine (i.e., animals) would render similar benefits in terms of pain management and/or rehabilitation.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A method of treating paresthesia in a peripheral nerve, comprising:
   locating the peripheral nerve that causing the paresthesia in the fascia layer of the skin; and
   injecting into a human in need of such treatment a therapeutically effective amount of a hyaluronic acid with a syringe needle directly against the peripheral nerve causing paresthesia.

2. The method of claim 1, wherein the hyaluronic acid is a non-avian based non-cross linked hyaluronic acid formulated to treat post-traumatic and degenerative joint disorders combined with an anesthetic.

3. The method of claim 1, wherein the hyaluronic acid is cross linked hyaluronic acid.

4. The method of claim 1, wherein administering to the human further comprises:
   determining a most reactive neural point overlying the peripheral nerve that produces a paresthesia in a painful area.

5. The method of claim 4, wherein administering to the human further comprises:
   isolating and marking an injection site with target marking lines at a reactive neural point overlying the peripheral nerve.

6. The method of claim 5, wherein administering to the human further comprises:
   preparing an epidermis with alcohol and performing a skin wheal.

7. The method of claim 5, wherein administering to the human further comprises:
   preparing an epidermis with alcohol and performing a skin wheal with a local anesthetic.

8. The method of claim 6, wherein administering to the human further comprises: introducing a regional nerve block; and utilizing a stimulator-guided local anesthetic and a cross linked hyaluronic acid delivery system.

9. The method of claim 8 wherein system settings in the stimulator-guided local anesthetic and cross linked hyaluronic acid delivery system are: output range of 0-5 mA; pulse width of 0.1 msec; stimulation frequency of 1 Hz; polarity positive and amperage is between 2.5 mA and 3 mA.

10. The method of claim 7, wherein the local anesthetic is 2% Lidocaine.

11. The method of claim 10, wherein administering to the human further comprises:
    performing a test injection with syringe filled with a compound to verify proper nerve selection.

12. The method of claim 11, wherein the compound is a 2% plain Lidocaine and 0.25% plain Bupivacaine.

13. The method of claim 11, wherein administering to the human further comprises:
    inserting a needle attached to the syringe filled with cross-linked hyaluronic acid through the skin wheal and past a reactive point; and
    injecting the cross-linked hyaluronic acid proximate the peripheral nerve.

14. The method of claim 13 wherein the needle is an atraumatic microcannulas having one, two or three side ports.

15. The method of claim 11 wherein a volume of cross-linked hyaluronic acid is 0.05-0.1 cc per aliquot.

* * * * *